United States Patent [19]

Griffith

[11] Patent Number: 4,518,779

[45] Date of Patent: May 21, 1985

[54] 1,2,3,4-TETRAHYDRO-1-AMINOMETHYL-4-PHENYL ISOQUINOLINES

[75] Inventor: Ronald C. Griffith, Pittsford, N.Y.

[73] Assignee: Pennwalt Corporation, Philadelphia, Pa.

[21] Appl. No.: 423,958

[22] Filed: Sep. 27, 1982

[51] Int. Cl.³ .................... C07D 217/14; A61K 31/47
[52] U.S. Cl. .................................................... 546/144
[58] Field of Search ......................................... 546/144

[56] References Cited

U.S. PATENT DOCUMENTS

| 3,420,818 | 1/1969 | Ott ........................... 546/144 |
| 3,435,038 | 5/1969 | Hardtmann et al. ........ 546/144 |
| 4,260,763 | 4/1981 | Bartmann et al. .......... 546/144 |
| 4,337,256 | 6/1982 | Suzuki et al. .............. 546/144 |
| 4,340,600 | 7/1982 | Brenner et al. ............ 546/144 |

Primary Examiner—Glennon H. Hollrah
Assistant Examiner—James H. Turnipseed

[57] ABSTRACT 1,2,3,4-Tetrahydro-1-aminomethyl-4-phenyl-isoquinolines useful as chemical intermediates and as pharmaceuticals and methods for their preparation.

14 Claims, No Drawings

1,2,3,4-TETRAHYDRO-1-AMINOMETHYL-4-PHENYL ISOQUINOLINES

BACKGROUND OF THE INVENTION

The present invention relates to new 1,2,3,4-tetrahydro-1-aminomethyl-4-phenyl-isoquinolines and to their methods of preparation.

SUMMARY OF THE INVENTION

The present invention pertains to a 1,2,3,4-tetrahydro-1-aminomethyl-4-phenyl-isoquinoline of formula I

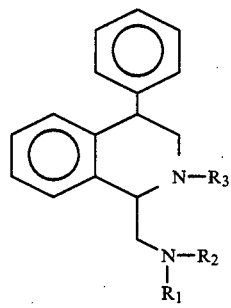

wherein $R_1$, and $R_2$ are from the class of hydrogen and lower alkyl, and $R_3$ is from the class of hydrogen, formyl and lower alkyl.

By the term "lower alkyl" as used herein is intended an alkyl group, straight or branched, containing about seven or less carbon atoms.

DETAILED DESCRIPTION OF THE INVENTION

It has been found that compound of formula I, and its addition salts in cis or trans form is useful as a chemical intermediate and possesses useful pharmacological properties, particularly anti-depressant, antihistaminic and cholinergic agonist or antagonist activity.

Processes for the preparation of compounds of formula I include steps (a) through (d) of Procedure A or steps (a) through (d) of Procedure B.

Procedure-A (a) React 2,2-diphenylethylamine of formula II,

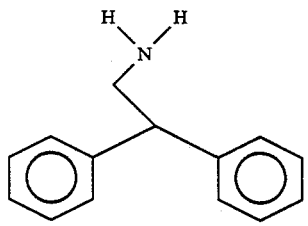

with an acylating agent, $XCH_2COX$, in which the substituents X are identical or different and represent groups which can be exchanged for an amino group, for example, X may be halogen, hydroxyl, methanesulfonate, tosylate, and in a preferred embodiment X is halogen, preferably chlorine. The reaction of these compounds is conducted in a manner conventional for nitrogen acylation in the presence of a base, such as sodium or potassium hydroxide, sodium or potassium carbonate, triethylamine, or pyridine, and can be done without solvents or preferably in a suitable solvent, for example, chloroform or methylene chloride. An appropriate temperature range is from $-15°$ C. to $+50°$ C. over a period of about 0.5 to 24 hours. The corresponding nitrogen acylated products III are thus obtained.

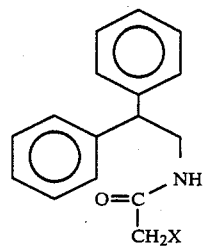

(b) Cyclize the compound of formula III according to Bischler-Napieralski conditions (*Organic Reactions*, Vol. VI, pp. 74–150. Ed. by Adams, et al.) to give the 1-(substituted methylene)-3,4-dihydro-4-phenylisoquinolines IV,

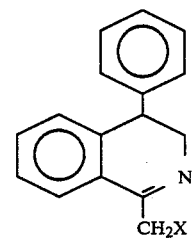

This reaction is conducted with an excess of dehydrating agent at elevated temperatures, preferably near the boiling point of the solvent for periods of from 0.5 to 24 hours. Examples of dehydrating agents are phosphorus pentoxide, phosphorus oxychloride, phosphorus pentachloride and polyphosphoric acid. The solvents are chosen from those which are inert to the reagents and afford a high enough temperature to promote the cyclization.

A preferred combination is phosphorous pentoxide in xylene at 140° C. for 2 hours.

(c) React a compound of formula IV with a primary or secondary amine, $R_1R_2NH$, where $R_1$ and $R_2$ have the values given for formula I, which displaces the leaving group X to give a 1-aminomethyl-3,4-dihydro-4-phenylisoquinoline V,

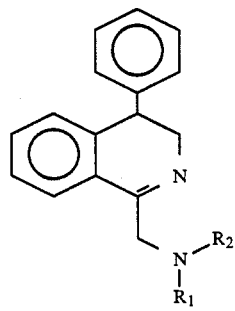

This reaction can be conducted with equimolar proportions of IV and the amine or in the presence of an excess of the amine. In the case of primary amines, $R_1NH_2$, a large excess of amine is advantageous to prevent disubstitution of the amine function. The reactions may be carried out in the absence of a solvent or with a solvent such as methanol and ethanol. The reaction can usually be conducted at temperatures from 0° to 60° C. but higher and lower temperatures may be used, and the period of the reaction may be from about 0.5 hours to 72 hours.

(d) Reduce the relatively unstable compounds of formula V in neutral or basic media in situ to the 1-aminomethyl-1,2,3,4-tetrahydro-4-phenylisoquinoline of formula I. These reductions are accomplished either by catalytic hydrogenation over catalysts such as palladium, platinum or nickel at pressures from about 5 psi to 60 psi and temperatures of from about 15° C. to 50° C. over a period of about 0.5 hours to 48 hours; or by complex hydride reducing agents such as sodium borohydride.

The products of this reaction sequence are normally mixtures of the cis and trans stereoisomeric forms of formula I ($R_3=H$). The relative amounts of isomers vary with the nature of the substituent, $R_1$, and $R_2$ and the reducing agent used to reduce the 1,2-double bond of V, and may also be affected by the nature of the solvent media in which the reductions are conducted. The proportions of the isomers may be determined by chromatographic or spectroscopic techniques and their separation into the pure stereoisomeric forms can be accomplished by conventional recrystallization or chromatographic methods.

An alternative method for the production of compounds of formula I comprises Procedure B below

Procedure-B (a) React 2-hydroxy-1,2-diphenylethylamine of formula VI

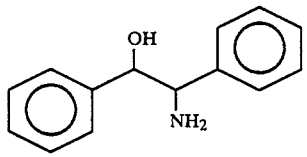

with an acylating reagent, $XCH_2COX$, in which X is the activated leaving groups defined previously and under conditions similar to those described in step (a), of Procedure A to give the N-acylated derivative VII

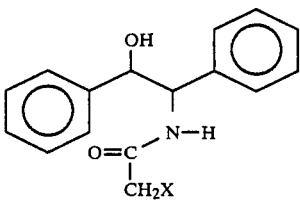

(b) Cyclize the compound of formula VII according to the Pictet-Gams modification (*Organic Reactions*, Vol. VI, pp. 76-78) of the Bischler-Napieralski reaction to produce the 1-(substituted methylene)-4-phenylisoquinoline (formula VIII), as a result of concomitant elimination of the 2-hydroxyl group and the apparent migration of the 1-phenyl group of the N-acyl-2-hydroxyl-1,2-diarylethylamine (N. Ardabilchi and A. O. Fitton, *J. Chem. Research(S)*, 310 (1979).

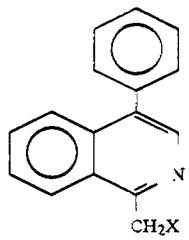

(c) React the compound of formula VIII with a primary or secondary amine $R_1R_2NH$ as described in paragraph (c), of Procedure A to give the 1-aminomethyl derivatives of formula IX.

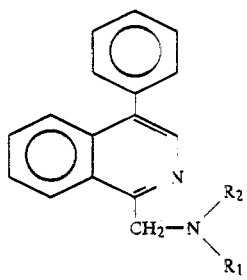

(d) Reduce catalytically or by complex hydride reduction the compounds of formula IX under conditions which reduce only the heterocyclic ring to produce compounds of formula I ($R_3=H$).

The compounds of formula I where $R_3$ is other than hydrogen and $R_1$ and $R_2$ are not hydrogen can be produced by reacting the compounds of formula I, where $R_3$ is hydrogen and $R_1$ and $R_2$ are other than hydrogen, further with alkyl or aralkyl halides or acyl halides or an equivalent reagent containing a leaving group replaceable by an amine function to produce 2-alkyl or 2-acyl-4-phenyl-1-aminomethyl-1,2,3,4-tetrahydroisoquinolines. Where the 2-substituent is acyl, the newly formed amide group can be further reduced with a complex hydride reagent. The alkylating or acylating reagents are normally used in slight excess in the presence of a base and can be reacted in the presence or absence of an inert solvent.

Illustrative techniques and processes for the preparation of the compound of formula I is presented in the following specific non-limiting Examples. Temperatures are in degrees centigrade unless otherwise indicated. The antihistaminic activity as reported in the Examples was determined by in vitro inhibition of histamine-stimulated adenylate cyclase (ad. cyc H) by the method developed by Kanof and Greengard, (*Nature*, 272, p. 329, 1978), and by in vitro inhibition of the specific binding of tritiated mepyramine ([$^3$H]-mepyramine) in brain as described by Tran, et al., (*Proc. Nat'l. Acad. Sci.* USA, 75 p. 6290, 1978). Cholinergic activity was determined by in vitro inhibition of the binding of tritiated quinuclidinyl benzylate ([$^3$H]-QNB) in brain as described by Yamamura and Snyder, (*Proc. Nat'l. Acad. Sci.* USA, 71 p. 1725, 1974). Antidepressant activity was determined in vitro by comparing the measured cholinergic and antihistiminic activities as described above with that of standard tricyclic antidepressant drugs such as imipramine, amitriptyline and doxepin, as well as the atypical antidepressant standards mianserin and iprindole. Further, antidepressant activity was determined in vivo by computer analysis of the EEG's of conscious beagles by the method described by Frankenheim, J., et al., (*Pharmacologist* 22, p. 298, 1980). These observations are reported in various Examples which follow in terms of "potency" where potency is expressed as the molar concentration required to inhibit by 50% the stimulation of adenylate cyclase observed after treatement with histamine (ad cyc H), or the binding of [$^3$H]mepyramine or [$^3$H]QNB to rate brain homogenates. The smaller numbers indicate greater potency. Each compound tested had an (ad cyc H) rating exceeding $1 \times 10^{-5}$ Molar.

EXAMPLE 1

Synthesis of Cis and Trans-1,2,3,4-Tetrahydro-1-methylaminomethyl-4-phenylisoquinoline dihydrochloride

Method A

N-Chloroacetyl-2,2-diphenylethylamine

To a stirred solution of 2,2-diphenylethylamine (100.0 g, 0.5 m) and triethylamine (123.0 g, 1.2 m) in chloroform (2 liters) maintained under nitrogen at ambient temperature was added dropwise chloroacetylchloride (124.2 g, 1.1 m) and the mixture stirred for 2 hours. Thin layer chromatography (TLC) analysis showed the reaction to be complete. The mixture was transferred to a separatory funnel and washed with 10% HCl (3×1 liter) and water (1 liter) and the organic phase dried over MgSO$_4$. The solvent was evaporated to a dark oil which was treated with cyclohexane (1 liter) and, upon standing, a solid crystallized which was collected by filtration, washed with cyclohexane and air dried to give 122.0 g of N-chloroacetyl-1,1-diphenylethylamine as a tan solid, m.p. 73°–74°.

1-Chloromethyl-3,4-dihydro-4-phenylisoquinoline hydrochloride

A stirred suspension of phosphorus pentoxide (373.0 g, 2.6 m) in xylene (8 liters) maintained under nitrogen was heated to a gentle reflux (ca 140°) and then treated portionwise with N-chloroacetyl-1,1-diphenylethylamine (90.0 g, 0.328 m) and the mixture maintained at reflux for 2 hours, then allowed to cool to ambient temperature overnight. The xylene was decanted off, the reaction flask was cooled in an ice bath, and the solid residue carefully treated with water (10 liters). This mixture was stirred for 0.5 hour, then basified to pH 11 with 50% NaOH, and extracted with chloroform (3×3 liters) and the extracts dried over MgSO$_4$. The solvents were evaporated to a dark oil which was immediately dissolved in a mixture of acetone (500 ml) and ether (200 ml) and acidified with HCl gas. Upon standing, a solid crystallized which was collected by filtration and air dried to give 88.1 g of 1-chloromethyl-3,4-dihydro-4-phenyl-isoquinoline hydrochloride, m.p. 206°–207°.

Cis and trans-1,2,3,4-tetrahydro-1-methylaminomethyl-4-phenylisoquinoline dihydrochloride To a stirred solution of methanol (1 liter) and monomethylamine (300 ml) maintained under nitrogen and cooled in an ice bath was added portionwise 1-chloromethyl-3,4-dihydro-4-phenylisoquinoline hydrochloride (83.0 g, 0.28 m) and the mixture heated to reflux (ca 50°–55°) for 2 hours. After cooling, the solution was poured into a pressure bottle and hydrogenated on a Parr apparatus over 5% Pd/C catalyst (5.0 g) at 40 psi for 16 hours. The catalyst was removed by filtration and the solvent evaporated to a gummy residue. This was dissolved in a mixture of methanol (200 ml) and isopropanol (200 ml) and acidified with HCl gas. Upon cooling and standing, a white solid crystallized which was collected by filtration and dried to give 64.0 g of the major isomer cis-1,2,3,4-tetrahydro-1-methylaminomethyl-4-phenylisoquinoline dihydrochloride, m.p. 276°–277°. A second crop of solid was obtained from the crystallization (26.1 g) which consisted (TLC) mostly of the minor isomer. Two recrystallizations of this crop provide the pure minor isomer trans-1,2,3,4-tetrahydro-1-methylaminomethyl-4-phenylisoquinoline dihydrochloride, m.p. 269°–270°.

Method B

N-Chloroacetyl-2-hydroxy-1,2-diphenylethylamine

To a stirred solution of 2-hydroxy-1,2-diphenylethylamine (95.5 g, 0.39 m) (obtained by catalytic reduction of benzoin oxime) and triethylamine (43.3 g, 0.429 m) in chloroform (1 liter) maintained under nitrogen was added dropwise chloroacetylchloride (46.2 g, 0.41 m) and the mixture heated to reflux for 1 hour. After cooling, the mixture was washed with 10% HCl (1 liter) and water and the organic phase dried over MgSO$_4$. The solvent was evaporated to a solid residue which was recrystallized from methanol to give 91.0 g of N-chloroacetyl-2-hydroxy-1,2-diphenylethylamine, m.p. 166°–169°.

1-Chloromethyl-4-phenylisoquinoline

A stirred suspension of phosphorus pentoxide (154.2 g, 1.1 m) in xylene (2 liters) maintained under nitrogen was heated to a gentle reflux (ca 140°) and then treated portionwise with N-chloroacetyl-2-hydroxy-1,2-diphenylethylamine (37.9 gm, 0.135 m) and the mixture maintained at reflux for 2 hours, then allowed to cool to ambient temperature overnight. The xylene was decanted off, the reaction flask was cooled in an ice bath, and the solid residue carefully treated with water (2 liters). The mixture was basified to pH 11 with 50% NaOH and extracted with ether (3×500 ml) and the extracts dried over MgSO$_4$. Evaporation of the solvents gives 24.3 g of 1-chloromethyl-4-phenylisoquinoline as an oil. This material was used as is for further processing. An analytical sample, obtained as the hydrochloride salt crystallized from acetone/ether, had m.p. 101°–102°.

1-Methylaminomethyl-4-phenylisoquinoline hydrochloride

To a stirred solution of monomethylamine (200 ml) and methanol (1 liter) maintained under nitrogen and cooled in an ice bath was added a solution of 1-chloromethyl-4-phenylisoquinoline (24.3 g, 0.093 m) in methanol (100 ml) and the mixture allowed to warm to ambient temperature and stirred for 3 days. The solvents were evaporated and the dark oily residue dissolved in methanol (50 ml) and isopropanol and acidified with HCl gas. Upon cooling and standing, a white solid crystallized which was collected by filtration and dried to give 16.3 g 1-methylaminomethyl-4-phenylisoquinoline hydrochloride, m.p. 212°–213°. An analytical sample, recrystallized from methanol/ethanol, had m.p. 215°–216°.

Cis and trans-1,2,3,4-tetrahydro-1-methylaminomethyl-4-phenylisoquinoline dihydrochloride A solution of 1-methylaminomethyl-4-phenylisoquinoline hydrochloride (29.0 g, 0.09 m) in 500 ml methanol and 500 ml water was hydrogenated in a Parr apparatus over 5% Pt/C (2.0 g) at 40 psi for 8 hours. TLC analysis revealed production of a ca 60/40 mixture of the isomeric reduction products. The catalyst was removed by filtration and the solvents evaporated to an oily residue which was dissolved in methanol (50 ml) and isopropanol (100 ml) and acidified with HCl gas to ensure excess. Upon cooling and standing, a white solid crystallized which was collected by filtration to give 19.8 g of a mixture of cis and trans-1,2,3,4-tetrahydro-1-methylaminomethyl-4-phenylisoquinoline dihydrochloride. Fractional recrystallizations from methanol/isopropanol produced the pure major (trans) isomer (9.2 g) and pure minor (cis) isomer (3.8 g) which were identical (ir, mp, nmr) with the materials obtained by Method A.

The ($^3$H)mepyramine rating for the cis form was $3.5 \times 10^{-6}$ Molar compared to $7.8 \times 10^{-8}$ Molar for the trans form; the ($^3$H)QNB for the cis form was $2.6 \times 10^{-6}$ Molar while the trans rating was $3.6 \times 10^{-6}$ Molar.

EXAMPLE 2

Synthesis of 1,2,3,4-Tetrahydro-1-dimethylaminomethyl-4-phenylisoquinoline dihydrochloride To a stirred solution of dimethylamine (250 ml) in methanol (1 liter) maintained under nitrogen and cooled in an ice bath was added portionwise 1-chloromethyl-3,4-dihydro-4-phenylisoquinoline (25.0 g, 0.084 m) and the mixture stirred for 4 hours while being allowed to warm to ambient temperature. The solution was poured into a pressure bottle and hydrogenated on a Parr apparatus over 5% Pd/C catalyst (5.0 g) at 40 psi. for 16 hours. The catalyst was removed by filtration and the solvent evaporated to a gummy residue. The residue was dissolved in methanol (300 ml) and isopropanol (100 ml) and acidified with HCl gas. Upon cooling and standing, a solid crystallized which was collected by filtration. Recrystallization from methanol/isopropanol/water gave 12.2 g of the major isomer of 1,2,3,4-tetrahydro-1-dimethylaminomethyl-4-phenylisoquinoline dihydrochloride as a monohydrate, m.p. 278°–279°.

The ($^3$H)mepyramine rating for the cis form was $2.8 \times 10^{-6}$ M while the ($^3$H)QNB rating was $4.0 \times 10^{-6}$ M.

EXAMPLE 3

Synthesis of 1,2,3,4-tetrahydro-2-methyl-1-dimethylaminomethyl-4-phenylisoquinoline dihydrochloride 1,2,3,4-Tetrahydro-2-formyl-1-dimethylaminomethyl-4-phenylisoquinoline To a stirred solution of 1,2,3,4-tetrahydro-1-dimethylaminomethyl-4-phenylisoquinoline base (Example 2) (9.5 g, 0.035 m) in toluene (100 ml) under nitrogen was added formic acid (8.05 g, 0.175 m) and the mixture heated to reflux in a Dean and Stark apparatus. After 3 ml of water were collected, the mixture was cooled, treated with 250 ml of 5% NaOH, and extracted with ether (1×150 ml) and then chloroform (3×100 ml) and the combined organic extracts dried over MgSO$_4$. Evaporation of the solvents gave 12.6 g of 1,2,3,4-tetrahydro-2-formyl-1-dimethylaminomethyl-4-phenylisoquinoline as a yellow oil. This material was used directly for additional chemical processing without further purification.

1,2,3,4-Tetrahydro-2-methyl-1-dimethylaminomethyl-4-phenylisoquinoline dihydrochloride To a stirred solution of 1 M borane in tetrahydrofuran (100 ml, 0.1 m) maintained under nitrogen was added 1,2,3,4-tetrahydro-2-formyl-1-dimethylaminomethyl-4-phenylisoquinoline (12.6 g, 0.04 m) and the mixture heated to reflux for 4 hours. The mixture was cooled in an ice bath and carefully treated with 200 ml of 10% HCl and refluxed for 1 hour. After cooling, the solvents were evaporated to dryness and the residue dissolved in water and extracted with chloroform with 50% NaOH, extracted with ether (3×150 ml), and the ether extracts dried over MgSO$_4$. Evaporation of the solvent at an aspirator gave 9.3 g of a pale yellow oily residue. This was dissolved in methanol (20 ml) and isopropanol (30 ml) and acidified with HCl gas. Upon cooling and standing, a white solid crystallized which was collected by filtration to give 5.0 g. Recrystallization from methanol/isopropanol and vacuum drying at 100° for 40 hours gave 4.2 g of 1,2,3,4-tetrahydro-2-methyl-1-dimethylaminomethyl-4-phenylisoquinoline dihydrochloride monohydrate, m.p. 186°–187°.

The ($^3$H)mepyramine rating for the cis forms was $1.8 \times 10^{-6}$ M while the ($^3$H)QNB rating was $1.2 \times 10^{-9}$ M.

EXAMPLE 4

Synthesis of 1,2,3,4-tetrahydro-1-(ethylamino)methyl-4-phenylisoquinoline dihydrochloride To a stirred solution of ethylamine (100 ml) in methanol (250 ml) maintained under nitrogen and cooled in an ice bath was added portionwise 1-chloromethyl-3,4-dihydro-4-phenylisoquinoline (10.0 g, 0.033 m) and the mixture heated to 50°–52° C. for 2 hours. After cooling, the solution was poured into a pressure bottle and hydrogenated on a Parr apparatus over 10% Pd/C catalyst (2.0 g) at 40 psi for 1 hour. The catalyst was removed by filtration and the solvent evaporated to a gummy residue. This residue was dissolved in methanol (50 ml) and isopropanol (50 ml) and acidified with HCl gas. Upon cooling and standing, a white solid crystallized which was collected by filtration. Recrystallization from methanol/isopropanol/water and vacuum drying gave 7.6 g of the major isomer of 1,2,3,4-tetrahydro-1-(ethylamino)methyl-4-phenylisoquinoline dihydrochloride, m.p. 241°–242°.

The ($^3$H)mepyramine rating for the cis form exceeded $1 \times 10^{-6}$ M while the ($^3$H)QNB was $7.0 \times 10^{-6}$ M.

The compound of formula I may be used in the form of pharmaceutical preparations which contain it in association with a compatible pharmaceutical carrier. The pharmaceutical preparations may be made up for enteral, (for example, oral) or parenteral administration. The dosage form may be a solution, suspension, tablet, capsule, powder or granule product of other suitable formulation.

It will be apparent, to those skilled in this art that many modifications and changes may be made in the invention described above without departing from the scope and spirit of the invention.

What is claimed is:
1. The compound

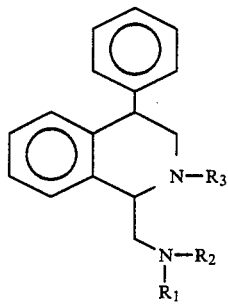

wherein $R_1$ and $R_2$ are from the class of hydrogen and lower alkyl, and $R_3$ is from the class of hydrogen, formyl, and lower alkyl and the pharmaceutically acceptable acid addition salts thereof.

2. The compound of claim 1 wherein $R_1$ is methyl and each of $R_2$ and $R_3$ is hydrogen.
3. The cis form of the compound of claim 2.
4. The acid addition salt of the compound of claim 3.
5. The trans form of the compound of claim 2.
6. The acid addition salt of the compound of claim 5.
7. The compound of claim 1 wherein $R_1$ and $R_2$ are methyl and $R_3$ is hydrogen.
8. The cis form of the compound of claim 7.
9. The acid addition salt of the compound of claim 8.
10. The compound of claim 1 wherein each of $R_1$, $R_2$ and $R_3$ are methyl.
11. The cis form of the compound of claim 10.
12. The compound of claim 1 wherein $R_1$ is ethyl and each of $R_2$ and $R_3$ is hydrogen.
13. The cis form of the compound of claim 12.
14. The acid addition salt of the compound of claim 13.

* * * * *